United States Patent [19] [11] E Patent Number: Re. 32,068
Ryan et al. [45] Reissued Date of Patent: Jan. 21, 1986

[54] DISTILLATIVE SEPARATION EMPLOYING BOTTOM ADDITIVES

[75] Inventors: James M. Ryan, Weston; John V. O'Brien, Shrewsbury, both of Mass.

[73] Assignee: Koch Process Systems, Inc., Westboro, Mass.

[21] Appl. No.: 704,180

[22] Filed: Feb. 22, 1985

Related U.S. Patent Documents

Reissue of:
[64] Patent No.: 4,428,759
Issued: Jan. 31, 1984
Appl. No.: 458,047
Filed: Jan. 14, 1983

[51] Int. Cl.[4] ..... F25J 3/04
[52] U.S. Cl. ..... 62/17; 62/20; 62/28
[58] Field of Search ..... 62/17, 20, 23-28; 55/68

[56] References Cited

U.S. PATENT DOCUMENTS 3,595,782 7/1971 Bucklin et al. ..... 62/23
4,035,167 7/1977 Starks ..... 62/17

*Primary Examiner*—Frank Sever
*Attorney, Agent, or Firm*—Richard P. Crowley

[57] ABSTRACT

An improved method for the distillation of a feed stream containing hydrocarbon components, which method is directed toward the production of a bottom product stream and an overhead product stream, both with desired specifications, which method comprises recycling a minor portion of the bottom product stream typically, but not necessarily, derived from said separation directly to a reflux condenser for the overhead product stream of said method, in order to effect a savings in energy in said distillative method, such as by adjusting the column operating conditions, such as the column operating pressure or the top or bottom operating temperatures of said column.

31 Claims, 3 Drawing Figures

CONDENSER
CONDENSER
CONDENSER
REBOILER
REBOILER
REBOILER
COOLER
COOLER
COOLER
$CO_2 + C_2 + C_3$
$CH_4$
$N_2 / CH_4$
$C_4 +$ ADDITIVE STREAM
$C_4 +$
$CO_2$
$C_2 +$
$CH_4$
$C_2 +$
$CO_2$
FEED
$CH_4$
$C_2 +$
$N_2$
$CO_2$
110
112
114
106
108
120
122
116
118
142
104
78
82
80
84
126
102
100
74
90
88
124
76
86
72
68
70
132
136
134
128
66
140
130
124
138
126
124

DISTILLATIVE SEPARATION EMPLOYING BOTTOM ADDITIVES

Matter enclosed in heavy brackets [ ] appears in the original patent but forms no part of this reissue specification; matter printed in italics indicates the additions made by reissue.

BACKGROUND OF THE INVENTION

It is desirable to operate distillative processes at minimum energy, to effect separation of the feed stream into a desired overhead product stream and a bottom product stream in a distillative column having vapor-liquid contacting devices, such as distillation trays, packing devices or a combination thereof. In typical distillative processes, the overhead product stream is at least partially condensed and a small portion recycled to the top of the distillative column, while the bottom product stream is withdrawn and reboiled and at least a portion recycled to the bottom of the column, to provide desirable column operating conditions. Some distillative columns operate under such conditions, so as to obtain the desired overhead product stream of defined specifications enriched in a desirable component, or conversely to obtain a bottom product stream of defined sepcifications enriched in a particular component, or both, so as to obtain purified streams for further separation or recovery or use in a chemical, refinery or petrochemical operation. In any event, such distillative techniques should be carried out at the most desirable column operating conditions, wherein optimum energy savings can be effected.

It is known that the separation of a feed stream in a distillative column, particularly a gaseous hydrocarbon feed stream comprising methane and an acid gas component, such as carbon dioxide, may be separated efficiently through the use of a nonpolar additive agent, such as a liquid additive agent; for example, a $C_3$–$C_6$ alkane, particularly butane-plus, introduced into the upper portion of said distillative column in an amount to prevent the formation of solids in the cryogenic distillation of methane from carbon dioxide, such as, for example, as more particularly set forth in U.S. Pat. No. 4,318,723, issued Mar. 9, 1982 (hereby incorporated by reference).

Also, it has been known that, in the prevention of azeotropic formation between ethane and carbon dioxide and ethylene and hydrogen sulfide and other components, the introduction of a nonpolar additive agent, such as a liquid hydrocarbon additive agent, such as a $C_3$–$C_6$ alkane, particularly butane-plus, prevents or inhibits the formation of azeotropes and enables the separation to provide an overhead product stream more enriched in a desirable component and a bottom product stream more enriched in a bottom product component, through the alteration of the azeotropic formation, such as, for example, as set forth and described more particularly in U.S. Pat. No. 4,350,511, issued Sept. 21, 1982 (hereby incorporated by reference).

Also, it is known to change the relative volatility of acid gas components, such as carbon dioxide to hydrogen sulfide, through the use of an additive agent, such as a nonpolar liquid additive agent, such as hydrocarbon; for example, a $C_3$–$C_6$ alkane, particularly butane-plus, in order to enhance the relative volatility of the carbon dioxide and hydrogen sulfide and, therefore, to increase the efficiency of separation, as set forth in U.S. Pat. No. 4,293,322, issued Oct. 6, 1981, now U.S. Pat. No. 4,383,842, issued May 17, 1983.

U.S. patent application Ser. No. 307,672, filed Oct. 1, 1981 (hereby incorporated by reference) relates to an improvement in the effective separation of methane from carbon dioxide in a distillative column, wherein the upper portion of the column is operated at temperatures above the triple point of carbon dioxide; that is, −70° F., by increasing the amount of nonpolar additive agent added to the reflux condenser, to maintain the reflux condenser and all portions of the column above the triplepoint temperature.

In all of the prior operations, the resulting bottom product stream contains, in addition to the usual bottom product stream components, a liquid nonpolar additive, particularly the liquid hydrocarbon additive added to change the operating conditions in the column. The liquid additive agent may be recycled with the bottom product stream or may be separated and recycled for use in any one or all of the aforementioned uses of an additive agent, particularly where such distillative processes are employed in one-, two-, three- or multiple-column operations for the separation of a natural gas stream or petro-chemical stream into the desired components. The feed streams employed in such distillation process include those streams which have major amounts of an acid gas component desired to be removed and those streams containing minor amounts of or even no acid gas components. It would be desirable, in such distillative separations or a combination of operations and other distillative operations where additives are not used, to reduce the energy requirements of such distillation techniques.

SUMMARY OF THE INVENTION

The invention relates to a distillative technique, wherein a product stream is employed to adjust distillative column operating conditions and to save energy. In particular, the invention concerns a distillative technique, wherein a small portion of a bottom product stream of defined specifications, typically a $C_3$–$C_6$ stream, is recycled to the condenser of a distillative column, wherein the overhead stream is not significantly contaminated by the recycled bottom product stream, to adjust column operating conditions and effect energy savings.

It has been discovered that the recycling of a portion of a column bottom product stream; for example, a minor amount, typically such as less than 30%; for example, 20%, and more typically about 1.0 to 10 mols of recycled product per 100 moles of feed stream, and introducing the recycled bottom product stream into the condenser employed for the column overhead stream of that or another column, or a plurality of distillative columns, permit the column operating conditions to be adjusted with a considerable savings of energy. It has been found that the recycling of the column bottom product stream to the reflux condenser of a distillation system permits the adjustment of column operating conditions, such as the raising of the top temperature of the column, the lowering of the bottom temperature of the column, or the lowering of the pressure of the column or lowering of the heating and cooling loads or a combination thereof, in order to permit the savings of energy.

In order to be effective in the practice of the invention, the introduction of the liquid additive agent into the condenser should be carried out, so as to provide that the additive agent is uniformly mixed with the overhead product stream from the distillative column entering the condenser, and typically to flow concurrently through the condenser with the overhead stream. It would be ineffectual to introduce the liquid additive agent to the condenser outlet and of considerably reduced efficiency to introduce the liquid additive poorly distributed into the inlet of the condenser. Therefore, the liquid additive should be introduced in and admixed with the incoming overhead product vapor stream and flow concurrently therewith, so that the liquid additive is generally uniformly distributed at least throughout the major portion of the heat-exchange surface or area of the condenser. One method of introducing and admixing is to employ a sparger adjacent the inlet of the condenser or adjacent or directly upstream of the heat-exchange surface of the condenser. Another suitable method of introducing and admixing comprises spraying the liquid additive concurrently into the incoming vapor overhead product stream.

One method of the invention is directed to those additive-recovery distillative techniques employing distillative columns, wherein the technique is directed toward mainly bottom-product-stream end specifications, and wherein the overhead product stream removes one or more contaminants or impurities from the feed stream. Thus, where the introduction of a bottom product stream; for example, a butane-plus stream, into a condenser, containing an overhead product stream, does not affect the operating specifications of the particular distillation technique, then the recycling of the bottom product stream into said condenser will permit the advantageous adjustment of the operating conditions of the column.

The invention is particularly useful wherein an additive agent is introduced into a column, to prevent the formation of a solids zone, to enhance the relative volatility of particular components, or to prevent azeotropic formation, such as those distillative techniques as described in the prior art in the Background of the Invention. The bottom product stream from the additive-recovery column of such operation can be recycled to the overhead condenser of the additive-recovery column or other column in the system to save energy.

The method of the invention is also of use wherein the feed stream comprises a hydrocarbon-containing stream, such as a petroleum or natural or synthetic gas stream high in hydrocarbons and which has a low amount of acid gas components or essentially few acid gas components. The invention is directed toward those bottom product streams, wherein the bottom product stream is typically enriched in higher alkanes and more particularly $C_4$-$C_6$ alkanes, such as $iC_4$, $nC_4$, $iC_5$, $nC_5$ and heavier hydrocarbon components. The recycling of the heavier hydrocarbon components of $C_4+$ directly from the bottom product stream into the overhead condenser of the distillation system provides for the overhead condenser to operate at a higher temperature, or alternatively the distillative column can be operated at a lower pressure, where the heavier components are present in the overhead product.

For example, in a feed stream which is low in acid gas components or contains essentially no acid gas components and wherein the bottom product stream is the desired stream of defined specifications and the overhead product stream is a stream containing undesired contaminants, the recycling of the bottom product stream directly from the bottom product stream, without separation into the overhead condenser employed for the overhead product stream, permits the temperature at the top of the column and of the condenser to increase, for example, from 10° F. to 60° F.; for example, 15° F. to 50° F., while providing for a reduction in temperature of the bottom of the column; for example, from 5° F. to 50° F. The column operating temperatures may be maintained and the overall column pressure reduced, all with the effective savings in energy, without affecting, or, in fact, in some cases increasing, the efficiency of separation of the bottom product stream. Also, the amount of the bottom product stream recycled may vary, to effect a reduction in column operating pressure of greater than 20 psi; for example, 30 psi, such as from 30 to 150 psi.

The method of the invention is advantageous where the feed stream comprises a butane-plus additive agent from a prior separation, and wherein the condenser of the distillative column is refrigerated by propane, ammonia or Freon (a trademark of du Pont Co.), and the bottom product additive is fed into the condenser, to raise the condenser temperature. The increase in temperature of the condenser permits the overhead product stream to be cooled or condensed employing a higher temperature; for example, the use of cooling water or any equivalent, cheap heat sink, providing increasing energy efficiency of the column operation.

For example, in one embodiment of the method of the invention, it is desirable to recover a bottom product stream containing $C_4+$ hydrocarbons; that is, the non-polar liquid additive agent from a prior operation, and not to separate such hydrocarbons, with the hydrocarbon bottoms having a hydrogen sulfide concentration kept below a given level; for example, 10 parts per million, and with $C_3$ removed to below a given level; for example, 0.5% by volume, and then to use the bottom product stream as at least a portion of a liquid additive stream in a cryogenic separation in another column. It has been found that the overhead stream is desirably cooled against water or an equivalent energy heat sink, by recycling a portion of the bottom product stream through the overhead condenser, so that the overhead condenser will operate at a higher temperature or, alternatively and preferably, the column can be operated at a lower pressure, if a sufficient amount of a heavier $C_4+$ hydrocarbons are in the overhead product stream.

In a further embodiment of the invention, such as in the separation of a substantially pure methane product stream from a natural gas feed stream containing nitrogen, such as from about 5% to 30% by volume or more nitrogen, the method provides for a residual gas stream of low carbon dioxide or hydrogen sulfide content, a fuel gas stream of low carbon dioxide, hydrogen sulfide and nitrogen content and a sour liquefied petroleum gas stream wiht a high ethane-plus recovery containing the bulk of the carbon dioxide and the hydrogen sulfide.

In this method, a natural gas feed stream containing nitrogen is introduced into a refrigerated distillative column, wherein a liquid additive is fed through the condenser to maintain ethylene-level refrigeration temperatures, and to wash the methane to the base of the column, with the overhead product stream being enriched in nitrogen. An additional refrigerated distillative column employing a liquid additive, such as in U.S. Pat. No. 4,318,723, issued Mar. 9, 1982, is employed to provide for the separation of a methane and carbon dioxide, with the carbon dioxide in the bottom product stream, together with the liquid additive of $C_4+$, and the methane removed from the overhead product stream, the formation of a solids zone prevented by the introduction of the liquid additive agent to the upper portion of the column. A third column for additive recovery is then employed, wherein the bottom product stream, containing the liquid additive, is employed as a refrigerated feed stream into the first and second distillative columns.

In a further embodiment, the separation of carbon dioxide and $C_2$ from $C_3+$ in a distillative column has been found to be enhanced significantly and considerable heat energy saved by the recycling of a minor amount of the bottom stream, such as the $C_4+$ bottom stream, from an additive-recovery column to the condenser or to the upper section of the column separating $CO_2$ and $C_3$. In order to obtain improved recovery of propane or reduction in energy, it is necessary that the nonpolar liquid $C_4+$ additive bottom agent be introduced a sufficient number of trays above the feed tray. The $C_4+$ bottom recycled stream may be added to the overhead condenser; however, some $C_4+$ stream will be produced or be present in the $CO_2$–$C_2$ overhead stream. If desired, to reduce the content of $C_4+$ stream in the $CO_2$–$C_2$ overhead stream, some or all of the $C_4+$ recycled bottom stream may be introduced into the uppermost tray section of the distillative column, so that the trays above will reduce the $C_4+$ content in the overhead stream. Typically, if the $C_4+$ recycled bottom stream is introduced into the upper section of the column, such introduction occurs in the first top ten trays of the column or less, such as the first top five or less trays. The reduction in heat removal is due to the improved relative volatility of the $CO_2$ to $C_3$ with the increased concentration of the $C_4+$ recycled bottom stream in the liquid in the column. This savings in heat energy generally occurs without significant changes in the overhead temperature and column operating pressure, due to the improved volatility ratio of the components.

This invention will be described for the purpose of illustration only in connection with certain specific embodiments; however, it is recognized that those persons skilled in the art may make various changes or modifications to such illustrated embodiments, all without departing from the spirit and scope of the invention.

DESCRIPTION OF THE EMBODIMENTS

Figure 1:
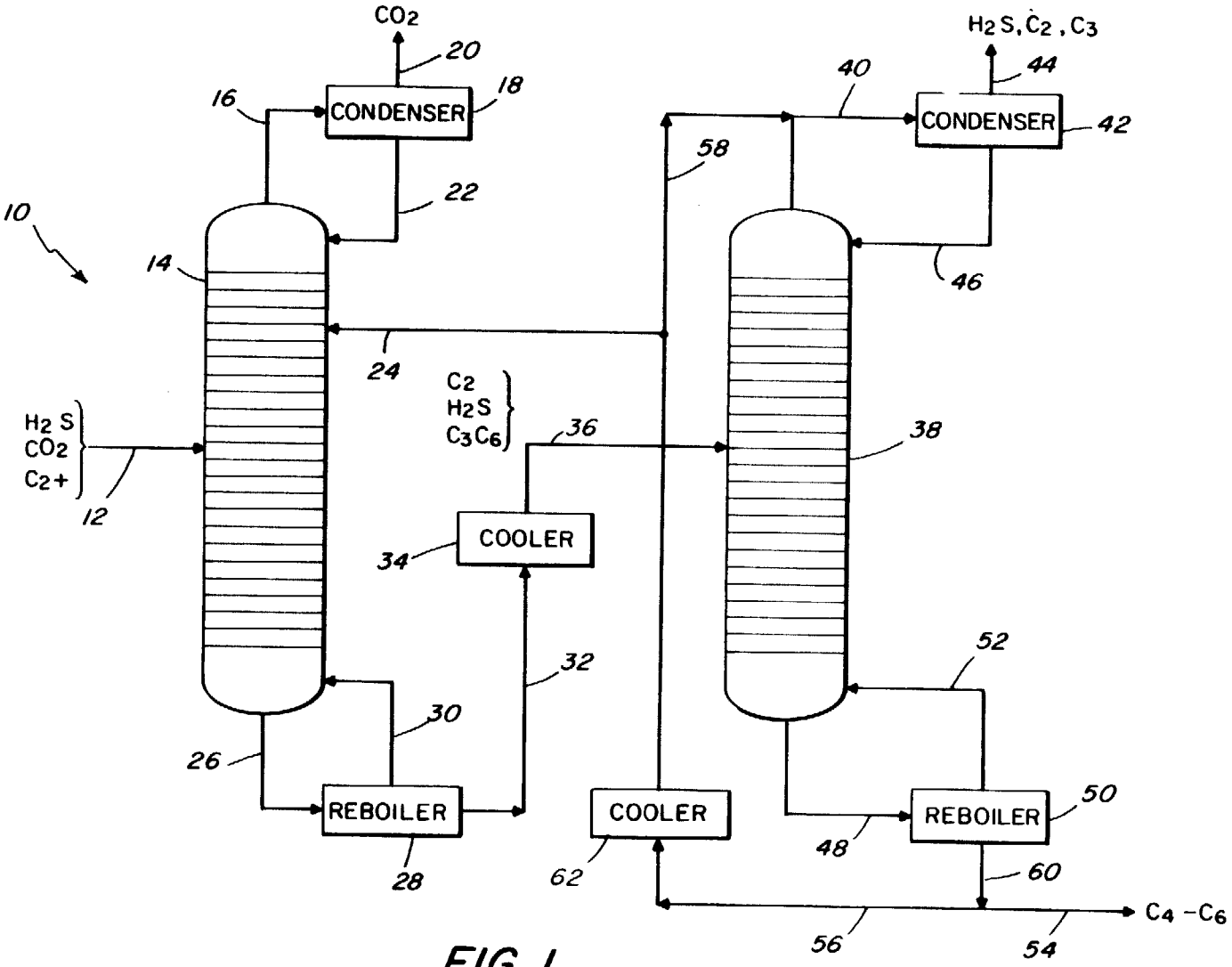
FIG. 1 is a schematic illustration of an application of the invention to additive recovery.

FIG. 1 is a schematic illustration of a distillative separation method employing the present invention of a nonpolar-liquid-agent additive-recovery application, wherein the feed stream is derived from one or more prior separation processes, and wherein the feed stream comprises hydrogen sulfide, carbon dioxide and $C_2+$ hydrocarbons introduced through line 12 into a distillative column 14 with vapor-liquid contact devices therein, such as distillation trays, and with a stream removed overhead through line 16 introduced into a reflux condenser 18 and a liquefied portion of the overhead stream recycled to the top of the column through line 22, while an enriched carbon-dioxide overhead product stream is removed overhead through line 20. In the operation of the column, a liquid additive, such as an alkane mixture; for example, $C_3$–$C_6$, comprising a major amount of butane-plus, is introduced into the upper section of the column 14 through line 24, to prevent or to modify azeotropic formations within the column 14. A column bottom stream is removed through line 26 and is introduced into a reboiler 28, and a portion is recycled through line 30 to the bottom of the column, while the bottom product stream, containing $C_2+$ and the $C_3$–$C_6$ additive and hydrogen sulfide, is withdrawn through line 32, is cooled in a heat exchanger 34 and is then introduced through line 36 as a feed stream into an additive-recovery distillative column 38 containing distillation trays.

An overhead product stream is removed through line 40 of column 38 and is introduced into a condenser 42, and a portion of the liquefied overhead stream is recycled to the top of the column through line 46, while an overhead product stream, containing $C_2$, $C_3$ and perhaps some very minor amounts of $C_4+$ and contaminants, such as hydrogen sulfide, is removed. A bottom product stream containing the $C_3$–$C_6$ additive agent is removed through line 48 into a reboiler 50, where a portion is recycled through line 52 to the bottom of the column, while another portion is removed by line 60 to line 56 through cooler 62 and is recycled and introduced concurrently directly by line 58 and line 40 into the inlet of the overhead reflux condenser 42 of column 38, to increase the operating temperature of the reflux condenser 42. The remaining portion of the defined bottom product stream containing $C_4+$ is removed through line 54. Optionally as illustrated, a further portion of the bottom stream is removed by line 24 from line 56 and is introduced as all or a portion of the additive agent introduced into column 14. Compositionally, it is not desired to separate the $C_3$–$C_6$ bottom stream, such as the $C_4+$ bottom stream or heavier components, and this stream may be recycled for use as an additive stream in one or more columns or merely recovered. The bottom product-recovery stream in the defined method is a specified stream having a hydrogen sulfide concentration kept below a defined specification level; for example, about 10 ppm or less of $H_2S$, and with $C_3$ removed to below a given specification level; for example, about 0.5% by volume or less. If operation of the column is desired with the same overhead condenser temperature, then the operating pressure of the column could be lowered.

In the method described in FIG. 1, the overhead reflux condenser 42 of the additive-recovery column 38 will operate at a higher temperature, or, alternatively, the distillative column 38 may be operated at a lower pressure, while maintaining the same overhead reflux condenser temperature. In the operation of column 38, the specifications are directed to the recovery of the additive agent as bottoms, so that the recycle of the additive bottom stream to the reflux condenser of the column does not contaminate the overhead product stream. The higher temperature of the overhead reflux condenser permits employing a less expensive cooling source, such as cooling water, air or a more moderate refrigerant source.

A number of computer simulations of the method were run, employing a plate-to-plate column calculator program, to simulate column condition and operation.

The software computer-program simulation employed was the Process SM Simulation Program of Simulation Sciences, Inc. of Fullerton, Calif., Version 0881. The composition of the feed, bottom, overhead and recycle additive agent streams in a representative computer simulation of the operation of an additive-recovery column, with recycle to the condenser of the additive-recovery column, such as column 38 of FIG. 1, is set forth in Table I for 100 psia operation.

The operation of the additive-recovery column at 100 psia, without any recycle of the additive agent to the reflux condenser 42 of the column 38, is illustrated by the data of Table II.

TABLE I

| | FLOW RATES - LB MOLS/HR | | | |
|---|---|---|---|---|
| Components | Overhead Stream (44) | Bottom Stream (60) | Feed Stream (36) | Recycle Liquid Stream (58) |
| $H_2S$ | 8.80 | 0.01 | 8.81 | 0.00 |
| $N_2$ | 0.00 | 0.00 | 0.00 | 0.00 |
| $CO_2$ | 17.6 | 0.00 | 17.6 | 0.00 |
| $C_1$ | 0.00 | 0.00 | 0.00 | 0.00 |
| $C_2$ | 123.13 | 0.09 | 123.22 | 0.00 |
| $C_3$ | 174.79 | 29.38 | 201.67 | 2.50 |
| $iC_4$ | 28.76 | 54.12 | 78.28 | 4.60 |
| $nC_4$ | 88.52 | 411.27 | 464.47 | 35.32 |
| $iC_5$ | 16.70 | 1263.12 | 1172.26 | 107.56 |
| $nC_5$ | 15.75 | 1868.65 | 1725.44 | 158.97 |
| $nC_6$ | 3.73 | 1673.61 | 1535.24 | 142.10 |
| $nC_7$ | 0.44 | 576.26 | 527.78 | 48.92 |
| Totals | 478.22 | 5876.53 | 5854.75 | 500.00 |
| Temperature Deg. F. | 109.00 | 232.80 | 210.00 | 232.70 |

TABLE II

| | | FLOW RATES - LB MOLS/HR | | | |
|---|---|---|---|---|---|
| Tray | Temp. Deg. F. Liquid | Vapor | Feeds | Products, BTU/hr | Duties mm |
| 1 | 93.3 | 1146 | | 0 (recycle feed) 462 (overhead net product) | 11.0 (condenser) |
| 2 | 139.0 | 1143 | 1608 | | |
| 3 | 161.1 | 1137 | 1605 | | |
| 4 | 173.4 | 1130 | 1599 | | |
| 5 | 181.1 | 1116 | 1592 | | |
| 6 | 187.4 | 1087 | 1578 | | |
| 7 | 195.2 | 1030 | 1549 | | |
| 8 | 208.0 | 6810 | 1492 | 5855 (feed) | |
| 9 | 213.0 | 6955 | 1417 | | |
| 10 | 216.5 | 7054 | 1563 | | |
| 11 | 219.3 | 7127 | 1661 | | |
| 12 | 221.9 | 7190 | 1735 | | |
| 13 | 224.7 | 7249 | 1797 | | |
| 14 | 228.6 | 7293 | 1856 | | |
| 15 | 236.9 | | 1900 | 5392 (bottom net product) | 19.0 (reboiler) |

The trays shown in Table II are theoretical or equivalent, perfect equilibrium trays, with the reflux condenser 42 as tray 1, the reboiler 50 as tray 15 and the feed stream introduced at tray 7.

The operation of the additive-recovery column at the same pressure, but with the recycle of the liquid additive stream to the reflux condenser in accordance with the invention, is illustrated by the data of Table III.

TABLE III

| | | FLOW RATES - LB MOLS/HR | | | |
|---|---|---|---|---|---|
| Tray | Temp. Deg. F. | Liquid | Vapor | Products, Feeds | Duties mm BTU/hr |
| 1 | 109.0 | 1738 | | 500 (recycle feed) 478 (overhead net product) | 13.9 (condenser) |

TABLE III-continued

| | | FLOW RATES - LB MOLS/HR | | | |
|---|---|---|---|---|---|
| Tray | Temp. Deg. F. | Liquid | Vapor | Products, Feeds | Duties mm BTU/hr |
| 2 | 141.2 | 1818 | 1716 | | |
| 3 | 156.8 | 1839 | 1797 | | |
| 4 | 167.1 | 1839 | 1818 | | |
| 5 | 175.6 | 1831 | 1818 | | |
| 6 | 183.5 | 1814 | 1810 | | |
| 7 | 192.3 | 1772 | 1792 | | |
| 8 | 204.9 | 7490 | 1750 | 5854 (feed) | |
| 9 | 209.4 | 7635 | 1614 | | |
| 10 | 212.4 | 7729 | 1759 | | |
| 11 | 214.9 | 7798 | 1853 | | |
| 12 | 217.2 | 7856 | 1921 | | |
| 13 | 219.8 | 7911 | 1980 | | |
| 14 | 223.8 | 7953 | 2034 | | |
| 15 | 232.8 | — | 2076 | 5876 (bottom net product) | 21.7 (reboiler) |

The effect of recycling 500-lb moles/hour of the $C_4+$ additive agent from the reboiler to the reflux condenser of the recovery column provides for an increase of the reflux condenser temperature from 93.3° F. without additive to 109.0° F. with the additive, and a decrease in the reboiler temperature from 236.9° F. to 232.8° F. This adjustment of the reflux condenser permits the overhead product stream to be cooled using cooling water or an equivalent, inexpensive heat sink, while the recycled additive agent does not contaminate the overhead stream, since the desired specification stream from the column is the $C_4+$ bottom product stream. If desired, the distillation could be operated at a lower pressure of 70 psia, if the reflux condenser is desired to be maintained at the same temperature as without additive. Thus, the data illustrate the significant advantage of saving energy by the recycling of the $C_4+$ liquid additive agent stream from the reboiler to the reflux condenser in the illustrated method of FIG. 1.

Figure 2:
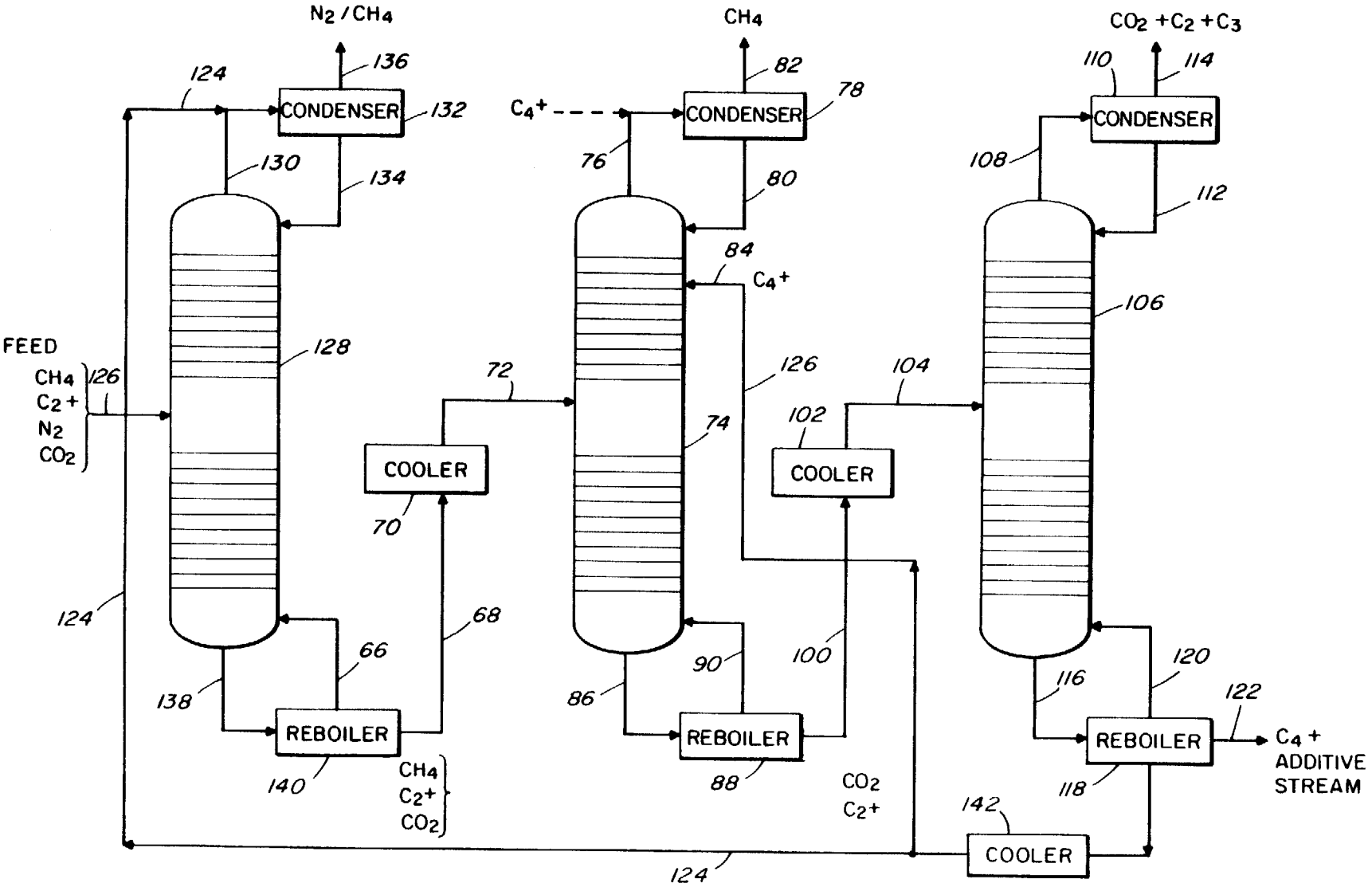
FIG. 2 is a schematic illustration of an application to a nitrogen separation method employing the invention.

FIG. 2 is a schematic illustration of another distillative separation employing the present invention, wherein a $C_3$–$C_6$ bottom product stream is recycled to the overhead of a column different from the column from which the bottom product stream is removed. In this embodiment, a feed stream, typically comprising a natural gas stream of a major amount of methane, some $C_2+$, nitrogen; for example, 9% to 25% nitrogen, and $CO_2$, is introduced by line 126 into a distillative column 128, and an overhead product stream is removed through line 130 and introduced into a condenser 132, and a portion of the liquefied, condensed stream is recycled through line 134 to the top of the column 128, while a mixture of essentially all nitrogen and part of the methane is removed as an overhead stream through line 136. A bottom product stream is removed through line 138 and is introduced into a reboiler 140, and a portion is recycled through line 66 to the bottom of the column 128. The bottom product stream, comprising part of the methane and practically all of the $C_2+$ and carbon dioxide, flows through line 68 into a heat exchanger 70, to cool the stream, which cool stream is introduced through line 72 as the feed stream into the next distillative column 74.

An overhead product stream is removed through line 76 and is introduced into a condenser 78, and a condensed portion is recycled to the top of the column 74 through line 80, while the overhead product stream of enriched, substantially pure methane is removed through line 82. In the operation of the column, a liquid additive $C_3$-$C_6$ alkane agent is added to the top of the column through line 84, to prevent the formation of a carbon-dioxide solids zone, as in U.S. Pat. No. 4,318,723. A bottom product stream is removed through line 86 and is introduced into a reboiler 88, and a portion is recycled through line 90 to the bottom of the column 74, and the bottom product stream from the reboiler, comprising carbon dioxide and $C_2$+ (with the additive agent), is removed through line 100 and is passed through heat exchanger 102, to cool the stream, and is introduced as a feed stream through line 104 into an additive-recovery distillative column 106. This column is operated as in FIG. 1, in order to provide a specified bottom product of essentially the liquid additive agent and to remove the carbon dioxide as an impurity in the overhead product stream.

An overhead product vapor stream, comprising carbon dioxide, $C_2$ and $C_3$, is removed from the top of the column through line 108 and is introduced into a reflux condenser 110, and a condensed portion is recycled through line 112 into the top of the column, while carbon dioxide, $C_2$ and $C_3$ are removed as an overhead stream from line 114. A bottom product stream, comprising primary $C_4$+, is removed from the bottom of the column through line 116 and is introduced into a reboiler 118, and a portion is recycled through line 120 to the bottom of the column 106. A specified bottom product stream, with defined specifications as in FIG. 1, is removed through line 122, while a portion thereof; for example, 0.5% to 20% or more; for example, 1.0% to 5% by moles relative to column feed, is continuously recycled through line 124 and cooler 142 and is introduced into condenser 132 of the distillative column 128, and a portion optionally may be introduced, via line 124 or 126 as shown, into condenser 78 (as illustrated by dotted lines), to increase the operating temperature of the condensers 132 and 78, thereby permitting a reduction in the operating pressure of columns 128 and 74 or a savings in heat energy. This operation permits the recovery of essentially all of the $C_2$, while $CO_2$ removal prior to the $N_2/CH_4$ separation is not required. In the process, the overhead temperature of the distillative column 128 can be raised independently of the overhead $N_2/CH_4$ content. The reflux condenser 132 temperature can be controlled and adjusted by the rate of the recycled additive addition to the condenser. In view of the very low boiling point of nitrogen removed in the overhead stream in column 128, the recycled additive rate may be set to require only an ethylene refrigeration system operating at about −125° F.

In a computer simulated example of the operation of distillative column 128 at 572 psia for the separation of $N_2$and $CH_4$, the compositions of the streams are set forth in Table IV, while the column operating conditions are set forth in Table V.

TABLE IV

| | FLOW RATES - LB MOLS/HR | | | |
|---|---|---|---|---|
| Components | Feed Stream (126) | Recycle Bottom Stream (124) | Overhead Stream (136) | Bottom Stream (68) |
| $N_2$ | 336.38 | 0.00 | 334.8 | 1.52 |
| $CO_2$ | 266.91 | 0.00 | 2.47 | 264.42 |
| CO | 6.21 | 0.00 | 6.08 | .13 |
| COS | .65 | 0.00 | .00 | .65 |
| $H_2S$ | 131.63 | 0.00 | .00 | 131.62 |
| $C_1$ | 2427.04 | 0.00 | 1637.02 | 790.07 |
| $C_2$ | 161.32 | 0.00 | .00 | 161.31 |
| $C_3$ | 126.87 | 27.38 | .44 | 153.81 |

TABLE IV-continued

| | FLOW RATES - LB MOLS/HR | | | |
|---|---|---|---|---|
| Components | Feed Stream (126) | Recycle Bottom Stream (124) | Overhead Stream (136) | Bottom Stream (68) |
| $iC_4$ | 50.01 | 130.37 | .59 | 179.78 |
| $nC_4$ | 75.39 | 196.65 | 49 | 271.54 |
| $iC_5$ | 40.25 | 105.17 | .07 | 145.35 |
| $nC_5$ | 7.60 | 19.72 | .00 | 27.31 |
| $nC_6$ | 15.21 | 39.98 | .00 | 55.19 |
| $nC_7$ | 10.85 | 28.48 | .00 | 39.34 |
| Totals | 3656.40 | 547.78 | 1982.07 | 2222.11 |
| Temperature Deg. F. | −80. | −120. | −125. | −48. |

TABLE V

| | FLOW RATES - LB MOLS/HR | | | | |
|---|---|---|---|---|---|
| Tray | Temp. Deg. F. | Liquid | Vapor | Products, Feeds | Duties mm BTU/hr |
| 1 | −125 | 1854 | | 548 (recycle feed) 1982 (overhead net product) | 2.9 (condenser) |
| 2 | −119 | 1870 | 3288 | | |
| 3 | −116 | 1802 | 3305 | | |
| 4 | −112 | 1700 | 3236 | | |
| 5 | −106 | 1580 | 3135 | | |
| 6 | −97 | 1466 | 3015 | | |
| 7 | −86 | 1437 | 2901 | 2481 (vapor feed) | |
| 8 | −81 | 2659 | 390 | 1175 (liquid feed) | |
| 9 | −78 | 2701 | 437 | | |
| 10 | −76 | 2730 | 479 | | |
| 11 | −73 | 2723 | 508 | | |
| 12 | −48 | | 501 | 2222 | 2.4 (reboiler) |

The addition of 548-lb moles/hour of the liquid bottom product from reboiler 118 to reflux condenser 132 in the separation of $N_2$ and $CH_4$ from the feed stream provided the recovery of 790-lb moles/hr of $CH_4$ with the bottom stream from column 128, which $CH_4$ is recovered as an essentially pure $CH_4$ overhead stream in column 74. The overhead product stream of column 128 is essentially over 99% a mixture of $N_2$ and $CH_4$. Without the introduction of the recycled $C_4$+ bottom additive stream, the reflux condenser temperature would be well below the limit (about −150° F.) of an ethylene refrigeration system, while, with the recycle of the bottom stream, the overhead temperature is −125° F., effecting a savings in heat energy in the operation of the column.

Figure 3:
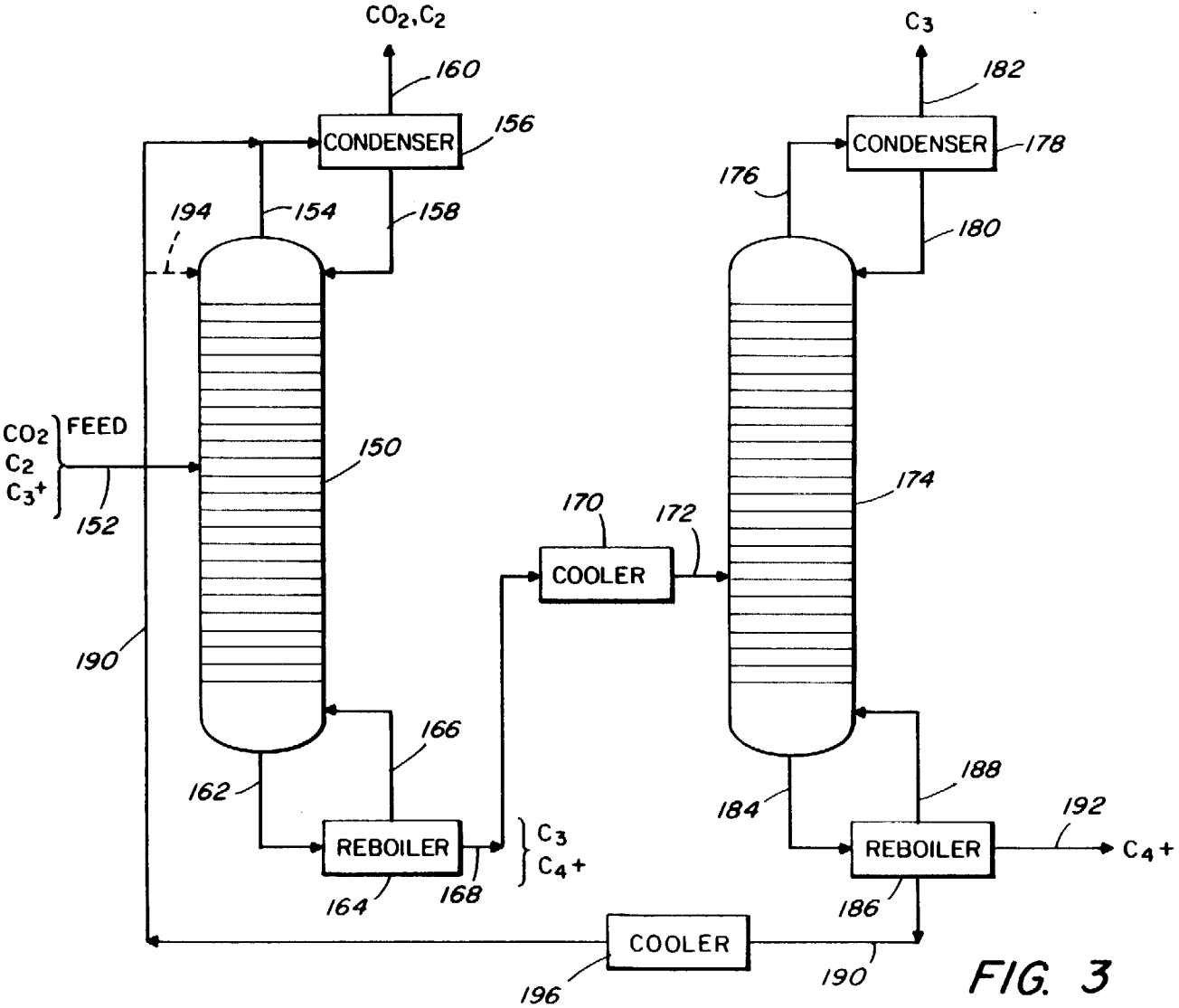
FIG. 3 is a schematic illustration of an application of $CO_2$-propane separation employing the invention.

FIG. 3 is a schematic illustration of a process of the invention, wherein the separation of $CO_2$ and ethane from propane by a distillative technique was discovered to be enhanced significantly by the introduction of small amounts of a liquid $C_4$+ additive recycled bottom stream to the condenser or to be uppermost tray section of the distillative separation column. The introduction of small amounts; for example, 1 to 8 mols, of a $C_4$+ bottom stream from the additive-recovery or other distillative column source per 100 mols of feed improves the relative volatility of the $CO_2$ to the propane with increased $C_4$+ fraction, and considerably reduces the heat duty on the reflux condenser and reboiler by over 60%.

In the embodiment shown in FIG. 3, a feed stream, consisting essentially of $CO_2$, ethane and $C_3$+, is introduced by line 152 in a distillative column 150 containing a plurality of distillation trays, and an overhead vapor stream is removed by line 154 and is introduced in a reflux condenser 156, and a portion of the liquid condensed stream is recycled through line 158 to the top of column 150. A mixture, composed essentially of $CO_2$ and ethane, is removed as an overhead product stream by line 160. A bottom product stream is removed by line 162 to a reboiler 164, and a portion is recycled through line 166 to the bottom of column 150. The bottom product stream, comprising primary propane, together with any recycled liquid additive agent introduced into the condenser or upper part of the column 150, is withdrawn by line 168 as a bottom product stream and is introduced into a heat exchanger 170 to cool the bottom product stream.

The cool bottom product stream is introduced by line 172 into the $C_4$+ additive-recovery column 174. An overhead product stream is removed by line 176 and is introduced into a condenser 178, and a portion from the condenser is recycled by line 180 into the top of the column 174. The overhead product stream, comprising primarily propane, is removed by line 182. A bottom product stream, comprising $C_4$+ additive agent, is removed by line 184 into reboiler 186, where a portion is recycled to the bottom of column 174 by line 188, and the $C_4$+ additive fraction is recovered by line 192 for recycle, recovery or for other use. A small portion of the recovered additive bottom product stream from column 174; for example, 1% to 5% by mol of the feed stream to separation column 150, is removed from the reboiler 186 by line 190 and is recycled through cooler 196 to the condenser 156 of separation column 150, and optionally, if desired, the liquid $C_4$+ additive bottom product stream also may be introduced into the uppermost tray section of the column 150 by line 194 shown as a dotted line.

In the operation of the separation column 150, Table VI shows a computer simulated data of the composition of the column feed stream comprising a major amount of $CO_2$, ethane and propane. The recycled additive-recovery column bottom additive stream from column 174, comprising primarily $C_4$–$C_6$ alkane liquid additive, is introduced in small amounts (less than about 4%; for example, 3%, by moles relative to the feed stream) by line 190 to the condenser 156 (tray 1), while the feed stream is introduced by line 152 to tray 7 of column 150. The overhead stream removes essentially all of the $CO_2$, $C_1$ and $C_2$ of the feed stream, while the bottom product stream is rich in the $C_3$+ components; that is, the separated $C_3$ and the recycled $C_4$+ additive bottom stream.

Table VII is the same as Table VI, except illustrating the feed, overhead and bottom stream compositions, wherein a recycled additive bottom stream is not employed in separation column 150.

TABLE VI

| | FLOW RATES - LB MOLS/HR | | | |
|---|---|---|---|---|
| Components | Feed (152) | Recycled Bottom Additive (190) | Overhead Stream (160) | Column Bottoms Stream (168) |
| $N_2$ | 0.59 | 0.0 | 0.59 | 0.00 |
| $O_2$ | 0.06 | 0.0 | 0.06 | 0.00 |
| $C_1$ | 60.70 | 0.0 | 60.70 | 0.00 |
| $CO_2$ | 247.04 | 0.0 | 246.97 | 0.06 |
| $C_2$ | 8.13 | 0.0 | 8.13 | 0.00 |
| $C_3$ | 7.04 | 0.0 | 0.71 | 6.33 |
| $iC_4$ | 0.75 | 1.30 | 0.20 | 1.85 |
| $nC_4$ | 2.00 | 3.46 | 0.32 | 5.14 |
| $iC_5$ | 0.39 | 0.68 | 0.02 | 1.05 |
| $nC_5$ | 0.36 | 0.62 | 0.01 | 0.96 |

TABLE VI-continued

| | FLOW RATES - LB MOLS/HR | | | |
|---|---|---|---|---|
| Components | Feed (152) | Recycled Bottom Additive (190) | Overhead Stream (160) | Column Bottoms Stream (168) |
| $nC_6$ | 2.27 | 3.92 | 0.05 | 6.14 |
| Totals | 329.39 | 10.00 | 317.81 | 21.57 |
| Temperature Deg. F. | 90 | 13 | 13 | 303 |

TABLE VII

| | FLOW RATES - LB MOLS/HR | | |
|---|---|---|---|
| Components | Feed Stream (152) | Overhead Stream (160) | Bottom Stream (168) |
| $N_2$ | 0.59 | 0.59 | 0.00 |
| $O_2$ | 0.06 | 0.06 | 0.00 |
| $C_1$ | 60.70 | 60.70 | 0.00 |
| $CO_2$ | 247.04 | 246.97 | 0.06 |
| $C_2$ | 8.13 | 8.13 | 0.00 |
| $C_3$ | 7.04 | 0.70 | 6.34 |
| $iC_4$ | 0.75 | 0.00 | 0.75 |
| $nC_4$ | 2.00 | 0.00 | 2.00 |
| $iC_5$ | 0.39 | 0.00 | 0.39 |
| $nC_5$ | 0.36 | 0.00 | 0.36 |
| $nC_6$ | 2.27 | 0.00 | 2.27 |
| Totals | 329.39 | 317.18 | 12.20 |
| Temperature Deg. F. | 90 | 12 | 255 |

Tables VIII and IX illustrate the operation of the $CO_2+C_2/C_3$ separation column 150 at 500 psia, both with and without the employment of and illustrating more particularly the change in the heat duty of the reboiler and condenser by the addition of the $C_4$+ recycled bottom additive stream to the condenser.

TABLE VIII

| | | FLOW RATES - LB MOLS/HR | | | |
|---|---|---|---|---|---|
| Tray | Temp. Deg. F. | Liquid | Vapor | Products, Feeds | Duties mm BTU/hr |
| 1 | 12.0 | 2516 | | 0 (recycle feed) 317 (overhead net product) | 11.6 (condenser) |
| 2 | 26.0 | 2612 | 2834 | | |
| 3 | 29.0 | 2628 | 2929 | | |
| 4 | 29.0 | 2631 | 2945 | | |
| 5 | 29.0 | 2634 | 2948 | | |
| 6 | 29.0 | 2639 | 2952 | | |
| 7 | 30.0 | 2645 | 2956 | | |
| 8 | 30.0 | 2588 | 2962 | 329 (feed) | |
| 9 | 32.0 | 2609 | 2576 | | |
| 10 | 33.0 | 2622 | 2597 | | |
| 11 | 33.0 | 2641 | 2610 | | |
| 12 | 34.0 | 2669 | 2629 | | |
| 13 | 35.0 | 2704 | 2657 | | |
| 14 | 40.0 | 2644 | 2693 | | |
| 15 | 61.0 | 2288 | 2631 | | |
| 16 | 116.0 | 2292 | 2276 | | |
| 17 | 164.0 | 2643 | 2280 | | |
| 18 | 193.0 | 2709 | 2631 | | |
| 19 | 219.0 | 2406 | 2697 | | |
| 20 | 255.0 | | 2394 | 12.20 (bottom net product) | 11.3 (reboiler) |

TABLE IX

| | | FLOW RATES - LB MOLS/HR | | | |
|---|---|---|---|---|---|
| Tray | Temp. Deg. F. | Liquid | Vapor | Products, Feeds | Duties mm BTU/hr |
| 1 | 13.0 | 1081 | | 10 (recycle feed) 318 (overhead net product) | 4.9 (condenser) |
| 2 | 25.0 | 1116 | 1389 | | |
| 3 | 27.0 | 1122 | 1424 | | |

TABLE IX-continued

| Tray | Temp Deg. F. | FLOW RATES - LB MOLS/HR Liquid | Vapor | Products, Feeds | Duties mm BTU/hr |
|---|---|---|---|---|---|
| 4 | 28.0 | 1123 | 1427 | | |
| 5 | 28.0 | 1125 | 1431 | | |
| 6 | 28.0 | 1127 | 1433 | | |
| 7 | 28.0 | 1129 | 1435 | | |
| 8 | 29.0 | 1066 | 1436 | 329 (feed) | |
| 9 | 32.0 | 1080 | 1044 | | |
| 10 | 33.0 | 1086 | 1053 | | |
| 11 | 34.0 | 1093 | 1064 | | |
| 12 | 35.0 | 1102 | 1071 | | |
| 13 | 37.0 | 1102 | 1081 | | |
| 14 | 47.0 | 998 | 1080 | | |
| 15 | 89.0 | 860 | 976 | | |
| 16 | 154.0 | 953 | 838 | | |
| 17 | 198.0 | 1045 | 931 | | |
| 18 | 229.0 | 1016 | 1023 | | |
| 19 | 263.0 | 943 | 995 | | |
| 20 | 303.4 | | 922 | 21.6 (bottom net product) | 4.7 (reboiler) |

As illustrated, a small amount of recycled $C_4+$ additive bottom stream markedly reduces the heat load on the condenser and reboiler, while significantly enhancing the separation of $CO_2$ from $C_3$, resulting not only in enhanced separation efficiency by a change in relative volatility, but accompanied by a savings in energy in the column operation.

The advantages of recycling the higher alkane bottom product stream of defined specifications and into an overhead condenser, wherein the bottom product stream does not constitute or serve as a contaminant for the overhead product stream, provide for energy savings.

What is claimed is:

1. In a method for the distillative separation, in a distillative column containing vapor-liquid contact devices, of a hydrocarbon-containing feed stream, which method comprises:

(a) introducing the feed stream into a distillative column operating under defined conditions of pressure, temperature and feed composition;

(b) withdrawing an overhead product stream encircled in at least one component to be removed from the feed stream;

(c) condensing at least a portion of the overhead product stream in a condenser and recycling a portion of the condensed overhead stream to the top portion of the said distillative column;

(d) recovering a bottom product stream with defined specifications enriched with at least one defined component of the feed stream for which recovery is sought; and (e) reboiling at least a portion of the withdrawn bottom product stream and recycling a portion of the bottom stream to the bottom portion of the column, the improvement which comprises introducing from about 1 to 30 mols per 100 mols of feed stream of a recycled liquid bottom product stream comprising [$C_3$-$C_6$] alkanes *having at least three carbon atoms* into an overhead condenser zone of the distillation column, the liquid bottom product stream introduced into the condenser zone concurrently and admixed with the overhead product stream in the condenser zone, the overhead product stream not being subject to substantial contamination by the recycled bottom product stream in the condenser zone, and the amount of the recycled bottom product stream sufficient, to provide adjusting of the operation condition of the distillation zone to effect a saving in the distillation column operating energy by:

(a) increasing the temperature of the condenser zone of the distillation column by about 10° F. or more; or (b) decreasing the temperature of the bottom of the distillation column by about 5° F. or more; or (c) reducing the distillation column operating pressure by about 20 psi or more.

2. The method of claim 1 wherein the amount of recycled liquid bottom product stream ranges from about 1 to 10 mols per 100 mols of feed stream.

3. The method of claim 1 which includes introducing sufficient, recycled, liquid bottom product stream into the overhead condenser zone, to increase the temperature of the overhead condenser zone from about 10° F. to 60° F. from the temperature of the overhead condenser zone, without the introduction of the bottom product stream.

4. The method of claim 1 which includes introducing sufficient, recycled, liquid bottom product stream into the overhead condenser zone, to permit the reduction in the distillative column operating pressure from the operating pressure employed, without the introduction of the bottom product stream.

5. The method of claim 4 which includes introducing sufficient bottom product stream, to reduce the operating pressure of the distillation column from about 30 to 150 psi.

6. The method of claim 1 wherein the recycled liquid bottom product stream comprises a majority of $C_4+$ alkanes.

7. The method of claim 1, which includes removing heat from the overhead condenser zone to which the bottom product stream has been added, by employing cooling water or a refrigerating system.

8. The method of claim 1 wherein the recycled liquid bottom product stream is recycled to the overhead condenser zone of the same distillative column from which the bottom product stream is recovered.

9. The method of claim 8 wherein the feed stream to the distillative column comprises a cool feed stream of $H_2S$ and $C_2+$ alkanes and is essentially free of carbon dioxide, and the overhead stream is enriched in $H_2S$, $C_2$ and $C_3$ and the bottom product stream is enriched in $C_4+$ alkanes.

10. The method of claim 1 wherein the recycled bottom product stream has less than about 0.5% mols of $C_3$ and a maximum of about 10 ppm of $H_2S$.

11. The method of claim 1 wherein the feed stream comprises $CO_2$, $H_2S$ and $C_2$–$C_6$ alkanes, and the bottom product stream comprises primarily $C_4$–$C_6$ alkanes.

12. The method of claim 1 wherein the feed stream is essentially free of acid gas components.

13. The method of claim 1 which includes introducing the liquid bottom product stream into the overhead condenser zone by sparging the liquid bottom stream into the vapor overhead product stream.

14. The method of claim 1 which includes spraying the liquid bottom stream concurrently into the vapor overhead product stream introduced into the overhead condensing zone.

15. The method of claim 1 for the distillative separation of carbon dioxide from a gaseous hydrocarbon feed stream containing carbon dioxide, which method comprises:

(a) introducing the feed stream into a first distillative column;

(b) introducing a nonpolar liquid $C_3$-$C_6$ alkane additive agent into the upper section of the column above the point of introduction of the feed stream;

(c) withdrawing a first overhead product stream from the top of the first column enriched in carbon dioxide;

(d) withdrawing a first bottom product stream from the bottom of the first column containing the liquid additive agent;

(e) introducing the first bottom product stream into a second distillative column as a feed stream for the second column;

(f) withdrawing from the top of the second column a second overhead product stream comprising primarily $C_2$ and $C_3$ alkanes;

(g) withdrawing from the bottom of the second column a second bottom product stream comprising primarily $C_4$+ alkanes;

(h) condensing at least a portion of the second overhead product stream in an overhead condenser and recycling a portion of the second overhead product stream to the top of the second column;

(i) reboiling at least a portion of the second bottom product stream in a reboiler and recycling a portion of the reboiled bottom product stream to the bottom of the second column;

(j) recovering a reboiled second bottom product stream comprising $C_4$+; and (k) recycling a portion of from about 1 to 30 mols of the second bottom product $C_4$+ stream, based on 100 mols of the feed stream in the second column, into the second overhead condenser and introducing the recycled $C_4$+ bottom stream concurrently with the second overhead product stream into the second overhead condenser, to increase the temperature of the second overhead condenser or to reduce the operating pressure of the first column.

16. The method of claim 15 which includes recycling a portion of the reboiled bottom product stream as at least a portion of the liquid additive stream introduced into the first column.

17. The method of claim 1 for the distillative separation of carbon dioxide from a gaseous hydrocarbon feed stream containing the carbon dioxide and $C_2$, $C_3$ and $C_4$+, which method comprises:

(a) introducing the feed stream into a first distillative column;

(b) withdrawing a first overhead product stream enriched in carbon dioxide and $C_2$ from the top of the first column;

(c) withdrawing a first bottom product stream enriched in $C_3$ from the bottom of the first column;

(d) condensing at least a portion of the first overhead product stream in a first overhead condenser and recycling a portion of the first overhead product stream to the top of the first column;

(e) reboiling at least a portion of the first bottom product stream in a reboiler and recycling a portion of the reboiled bottom product stream to the bottom of the first column;

(f) introducing a first bottom product stream as the feed stream into a second distillative column containing a plurality of distillation trays;

(g) withdrawing from the top of the second column a second overhead product stream comprising primarily $C_3$;

(h) withdrawing from the bottom of the second column a second bottom product stream comprising primarily $C_4$+;

(i) recovering a reboiled second bottom product stream; and (j) recycling a portion of from about 1 to 10 mols of the second bottom $C_4$+ product stream, based on 100 mols of the feed stream in the first column, into the inlet of the first overhead condenser concurrently with the first overhead product stream, to admix uniformly the bottom stream and overhead product stream in the condenser, or to the upper ten or less trays of the first column, to reduce the heat duty in the operation of the first column.

18. The method of claim 1 for the distillative separation of nitrogen and methane from a gaseous feed stream comprising nitrogen, methane, carbon dioxide and $C_2$+ alkanes, which method comprises:

(a) introducing the feed stream into a first distillative column;

(b) withdrawing from the top of the first column a first overhead product stream enriched in nitrogen;

(c) withdrawing from the bottom of the first column a first bottom product stream containing $CH_4$, $CO_2$ and $C_2$+;

(d) condensing at least a portion of the first overhead product stream in a first overhead condenser and recycling a portion of the condensed first overhead product stream to the top of the first column;

(e) introducing the first bottom product stream as a second feed stream into a second distillative column;

(f) withdrawing from the top of the second column a second overhead product stream enriched in methane;

(g) withdrawing from the bottom of the second column a second bottom product stream containing $CO_2$ and $C_2$+ products;

(h) introducing into the upper section of the second column, above the point of introduction of the second feed stream, a nonpolar, liquid, $C_3$-$C_6$ alkane additive agent;

(i) condensing at least a portion of the second overhead product stream in a second overhead condenser and recycling a portion of the condensed second overhead stream to the top of the second column;

(j) introducing the second bottom product stream as the third feed stream into a third distillative column;

(k) withdrawing from the top of the third column a third overhead product stream containing $CO_2$, $C_2$ and $C_3$;

(l) withdrawing and recovering a third bottom produce stream from the bottom of the third column composed primarily of $C_4$+ alkanes; and (m) recycling at least a portion of the third bottom product stream to the first overhead condenser concurrently with the first overhead product stream, to admix uniformly the bottom stream and overhead product stream in the condenser, to provide for an increase in the temperature of the overhead condenser or a reduction in the operating pressure of the first column.

19. The method of claim 18 which includes recycling a portion of the third bottom product stream for introduction as at least a part of the liquid additive agent into the second column.

20. The method of claim 18 wherein the first overhead product stream comprises essentially nitrogen and methane, and the second overhead product stream comprises essentially pure methane.

21. The method of claim 1 which includes introducing recycled liquid bottom product stream into the overhead condenser zone in an amount sufficient to reduce the operating temperature of the bottom of the column from about 5° to 50° F. from the temperature without the introduction of the recycled liquid bottom product stream.

22. The method of claim 1 which comprises the distillative separation in the distillation column of a carbon dioxide and $C_2$ overhead stream and a $C_3+$ bottom stream which includes recycling a minor amount of a bottom product stream into the uppermost tray section of the distillative column separating carbon dioxide and $C_2$ overhead stream from the $C_3+$ and bottom stream.

23. The method of claim 22 wherein the bottom product stream comprises a $C_4+$ stream and is introduced into at least one of the top ten trays of the distillation column.

24. The method of claim 1 which comprises the distillative separation of nitrogen and methane from a feed stream in a $CH_4$-$N_2$ distillative separation column and which includes introducing a liquid bottom product stream from the distillative separation of $CO_2$, $C_2$ and $C_3$ as an overhead stream and the $C_4+$ additive bottom product stream into the overhead condenser zone of the $CH_4$-$N_2$ distillation column for the separation of $CH_4$ and $N_2$ to increase the column operating temperature of the $CH_4$-$N_2$ overhead condenser zone.

25. The method of claim 1 which comprises the separation of a hydrogen sulfide, $C_2$ and $C_3$ stream as an overhead stream from a $C_4$-$C_6+$ liquid bottom product stream in a distillation column which includes recycling the $C_4$-$C_6+$ liquid bottom product stream into the overhead condenser zone of the distillation column to increase the temperature of the overhead condenser zone.

26. The method of claim 25 wherein from about 1 to 8 mols of the bottom product stream is recycled per 100 mols of feed stream to the $CO_2$-$C_2$ distillation column.

27. The method of claim 1 which comprises the distillative separation of carbon dioxide and ethane stream from propane stream which includes distillatively separating $CO_2$ and $C_2$ as an overhead stream in a distillation column and recovering a $C_3+$ bottom stream as a feed stream for distillatively separating in another distillation column of $C_3$ as an overhead product stream and $C_4+$ as a liquid bottom additive stream and recycling a portion of the liquid bottom product stream to the overhead condenser of the distillative column for the $CO_2$-$C_2$ separation from $C_3+$ to increase the operating temperature of the overhead condenser zone of the $CO_2$-$C_2$ distillation column.

28. The method of claim 1 wherein the bottom product stream is admixed with the overhead product stream upstream of the heat exchange area in the condenser zone so that the admixed overhead and the bottom product stream are generally uniformly distributed through the vapor portion of the heat exchange area of the condenser zone.

29. The method of claim 1 wherein the overhead condensing zone is maintained by the recycling of the bottom product stream at a temperature of about −125° F. or more.

30. The method of claim 1 which includes recycling the liquid bottom product stream from a different distillation column into the condenser zone of the distillation overhead column.

*31. The method of claim 1 wherein the recycled liquid bottom product stream comprises $C_3$-$C_7$ alkanes.*

* * * * *